(12) United States Patent
Cabrera et al.

(10) Patent No.: US 11,298,152 B2
(45) Date of Patent: Apr. 12, 2022

(54) TROCAR RETAINING MECHANISM INCLUDING BAND SUPPORT

(71) Applicant: Covidien LP, Mansfield, MA (US)

(72) Inventors: Ramiro Cabrera, Cheshire, CT (US); David E. Valentine, Hamden, CT (US)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 16/804,367

(22) Filed: Feb. 28, 2020

(65) Prior Publication Data

US 2021/0267628 A1   Sep. 2, 2021

(51) Int. Cl.
*A61B 17/34* (2006.01)
*A61B 17/115* (2006.01)
*A61B 17/00* (2006.01)

(52) U.S. Cl.
CPC ...... *A61B 17/3417* (2013.01); *A61B 17/1155* (2013.01); *A61B 2017/00486* (2013.01); *A61B 2017/3419* (2013.01)

(58) Field of Classification Search
CPC .................. A61B 17/3417; A61B 17/1155
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Fllipl |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Nathaniel C Chukwurah
(74) *Attorney, Agent, or Firm* — Carter, DeLuca & Farrell LLP (57) ABSTRACT

An adapter assembly for connecting a loading unit to a handle assembly includes a sleeve, a trocar assembly releasably securable with the sleeve, a drive assembly including at least one flexible band, and a trocar retaining mechanism configured to releasably secure the trocar assembly within the sleeve. The trocar retaining mechanism includes a band support configured to prevent buckling of at least one flexible band.

20 Claims, 10 Drawing Sheets

(56) References Cited

U.S. PATENT DOCUMENTS

| | | |
|---|---|---|
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Mien et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |

(56) References Cited

U.S. PATENT DOCUMENTS

| | | |
|---|---|---|
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |

(56) References Cited

U.S. PATENT DOCUMENTS

| | | |
|---|---|---|
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |

(56) References Cited

U.S. PATENT DOCUMENTS

| | | |
|---|---|---|
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0296234 A1* | 10/2016 | Richard ............ A61B 17/1155 |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

TROCAR RETAINING MECHANISM INCLUDING BAND SUPPORT

FIELD

The disclosure relates to reusable surgical stapling devices including a removable trocar assembly. More particularly, the disclosure relates to reusable adapter assemblies including a trocar retaining mechanism having band support.

BACKGROUND

Surgical devices for applying staples, clips, or other fasteners to tissue are well known. Typically, endoscopic stapling devices include an actuation unit, i.e., a handle assembly for actuating the device, a shaft for endoscopic access, and a tool assembly disposed at a distal end of the shaft. In certain of these devices, the shaft includes an adapter assembly having a proximal end securable to the handle assembly and a distal end securable to the tool assembly. The adapter assembly may include an extension.

In order to transfer force from the handle assembly to the tool assembly, adapter assemblies may include one or more drive assemblies in the form of flexible bands. Transferring force using flexible bands in compression may result in buckling of the flexible band. Therefore, it would be beneficial to have a mechanism for reinforcing the flexible bands to prevent buckling.

SUMMARY

An adapter assembly for connecting a loading unit to a handle assembly is provided. The adapter assembly includes a sleeve, a trocar assembly releasably securable with the sleeve, a drive assembly including at least one flexible band extending at least partially within the sleeve, and a trocar retaining mechanism configured to releasably secure the trocar assembly within the sleeve. The trocar retaining mechanism includes a band support positioned in engagement with the at least one flexible band to prevent buckling of the at least one flexible band.

In certain aspects of the disclosure, the band support includes a bottom surface in engagement with the at least one flexible band. The band support may include first and second support members in engagement with the at least one flexible band. The band support may include a cutout for accommodating the at least one flexible band.

In some aspects of the disclosure, the adapter assembly further includes a wire harness extending at least partially through the sleeve. The band support may define a channel for receiving the wire harness. The band support may include a lip on either side of the channel for maintaining the wire harness within the channel. The trocar retaining mechanism may further include a band guide defining a cutout for receiving at least one flexible band. The band guide may define a central opening for receiving the band support.

In aspects of the disclosure, the trocar retaining mechanism further includes a retaining block defining a longitudinal passage for receiving the trocar assembly. The trocar assembly may include a housing and a trocar member slidably disposed within the trocar assembly.

Also provided is a surgical stapling device including a handle assembly and an adapter assembly secured to the handle assembly. The adapter assembly includes a drive assembly including at least one flexible band extending at least partially through the adapter assembly. The adapter assembly further includes a retaining mechanism configured to releasably secure a trocar assembly within the adapter assembly. The retaining mechanism includes a band support positioned in engagement with the at least one flexible band to prevent buckling of the at least one flexible band.

In some aspects of the disclosure, the band support includes a bottom surface in engagement with the at least one flexible band. The band support may include first and second support members in engagement with the at least one flexible band. The band support may include a cutout for accommodating the at least one flexible band.

In certain aspects of the disclosure, the adapter assembly may further include a wire harness extending at least partially through the adapter assembly. The band support may define a channel for receiving the wire harness. The band support may include a lip on either side of the channel for maintaining the wire harness within the channel. The retaining mechanism may further include a band guide defining a cutout for receiving the at least one flexible band. The band guide may define a central opening for receiving the band support.

The adapter assembly may further include a trocar assembly. The retaining mechanism may include a retaining block defining a longitudinal passage for receiving the trocar assembly. The trocar assembly may include a housing and a trocar member slidably disposed within the trocar assembly.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects of the disclosure given below, serve to explain the principles of the disclosure, wherein.

DETAILED DESCRIPTION

Aspects of the disclosed adapter assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 1:
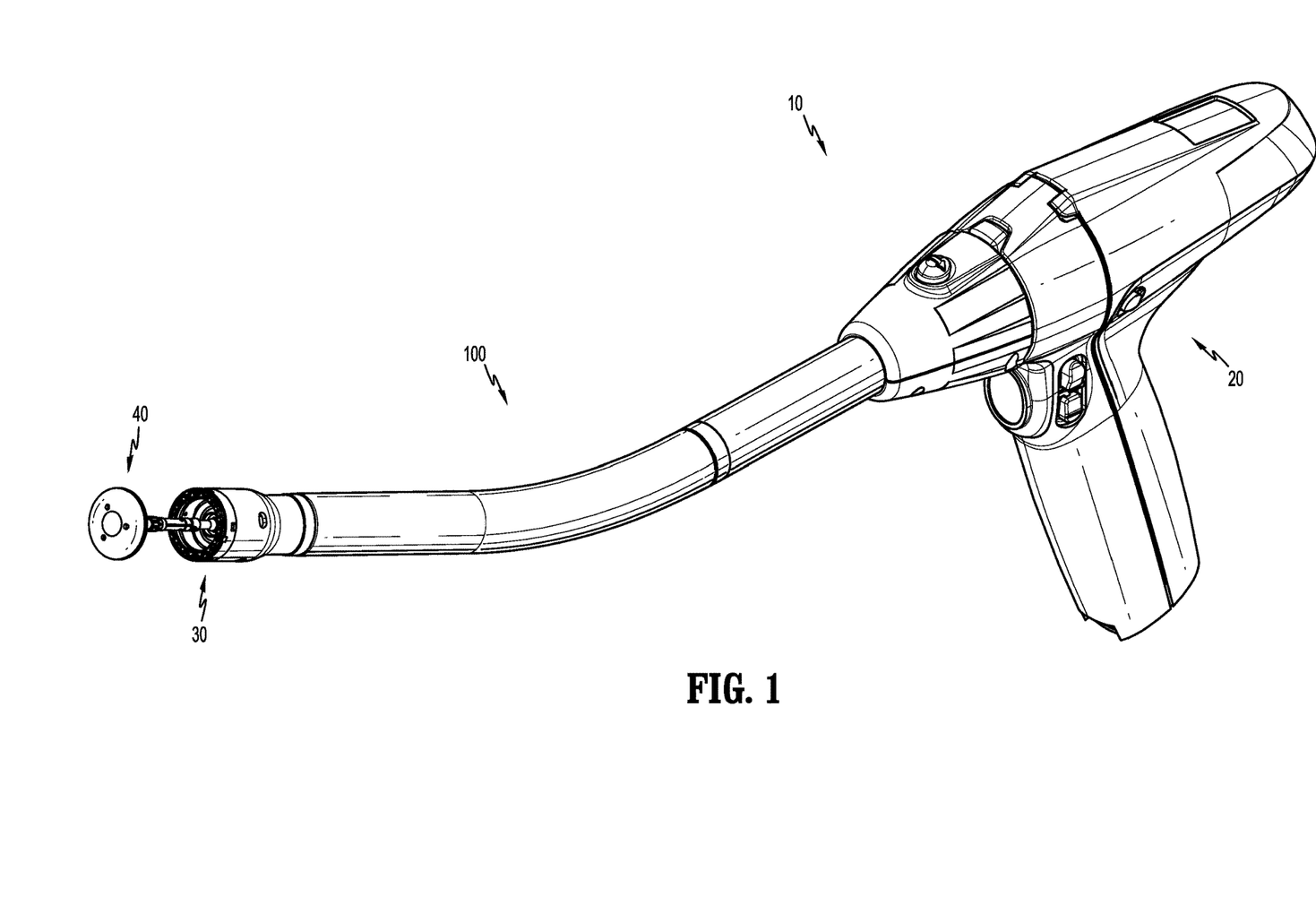
FIG. 1 is a perspective view of a surgical stapling device including an handle assembly with an adapter assembly according to aspects of the disclosure.

FIG. 1 illustrates an adapter assembly according to aspects of the disclosure, shown generally as adapter assembly 100, as a component of a surgical stapling device 10. The surgical stapling device 10 further includes a powered handle assembly 20, a loading unit 30, and an anvil assembly 40. Although shown and described with reference to a powered surgical stapling device 10, the aspects of the disclosure may be modified for use with manual surgical stapling devices having various configurations, and with powered surgical stapling devices having alternative configurations. For a detailed description of exemplary surgical stapling devices, please refer to commonly owned U.S. Pat. Nos. 9,023,014 and 9,055,943.

Figure 2:
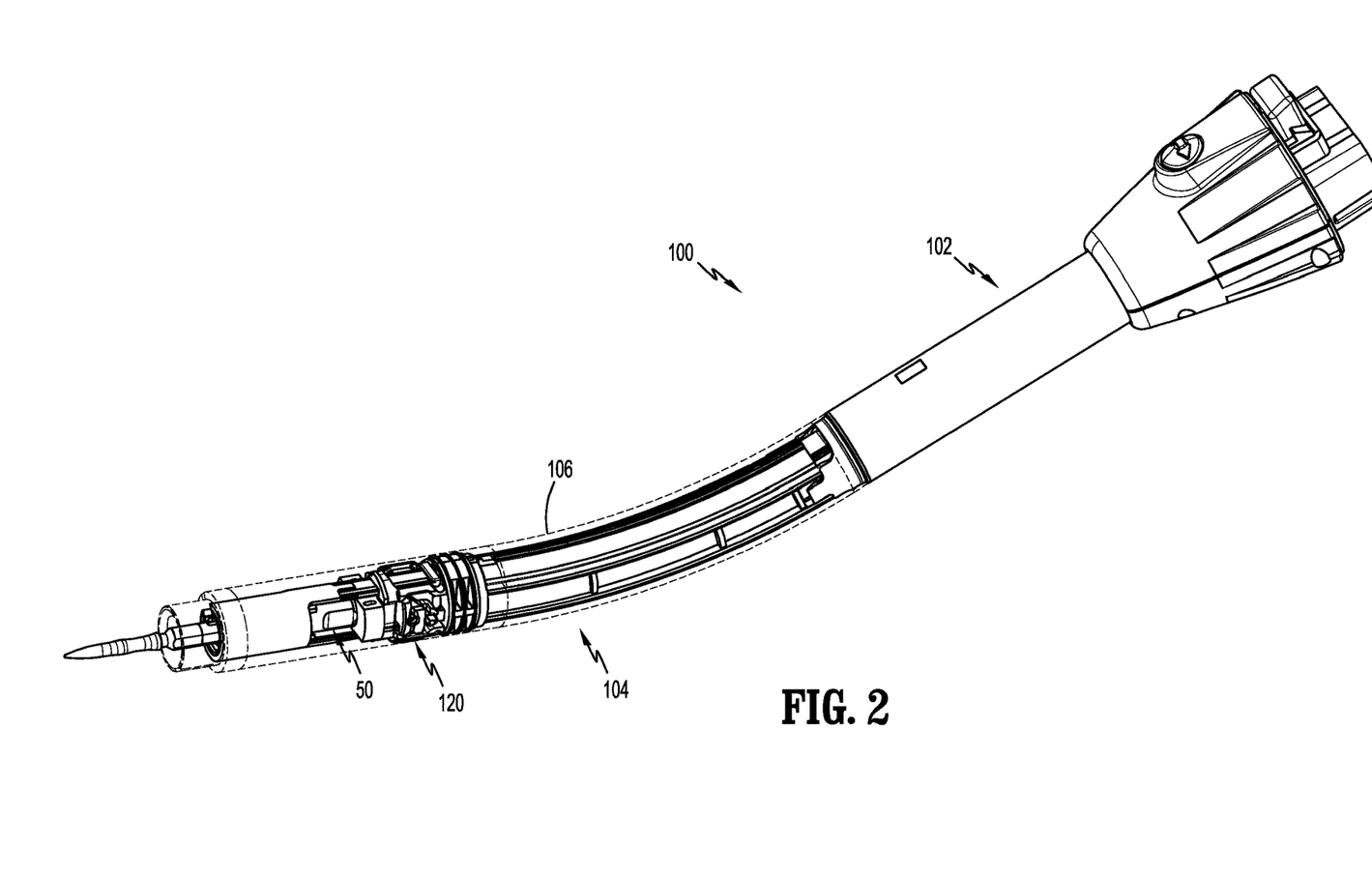
FIG. 2 is a perspective view of the adapter assembly shown in FIG. 1 with a removable trocar assembly extending from a distal end of the adapter assembly and an outer sleeve shown in phantom.

FIG. 2 illustrates the adapter assembly 100 of the surgical stapling device 10 (FIG. 1). The adapter assembly 100 will only be described to the extent necessary to fully disclose the aspects of the disclosure. For a detailed description of an exemplary adapter assembly, please refer to commonly owned U.S. Pat. No. 10,226,254 ("the '254 patent").

The adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another. A trocar assembly 50 is releasably secured within the distal portion 104 of the adapter assembly 100 and is configured for operable engagement with the anvil assembly 40. The distal portion 104 of the adapter assembly 100 includes inner and outer drive assemblies 110 (FIG. 3), 112 that are disposed within an outer sleeve 106 and are received through a trocar retaining mechanism 120.

Figure 3:
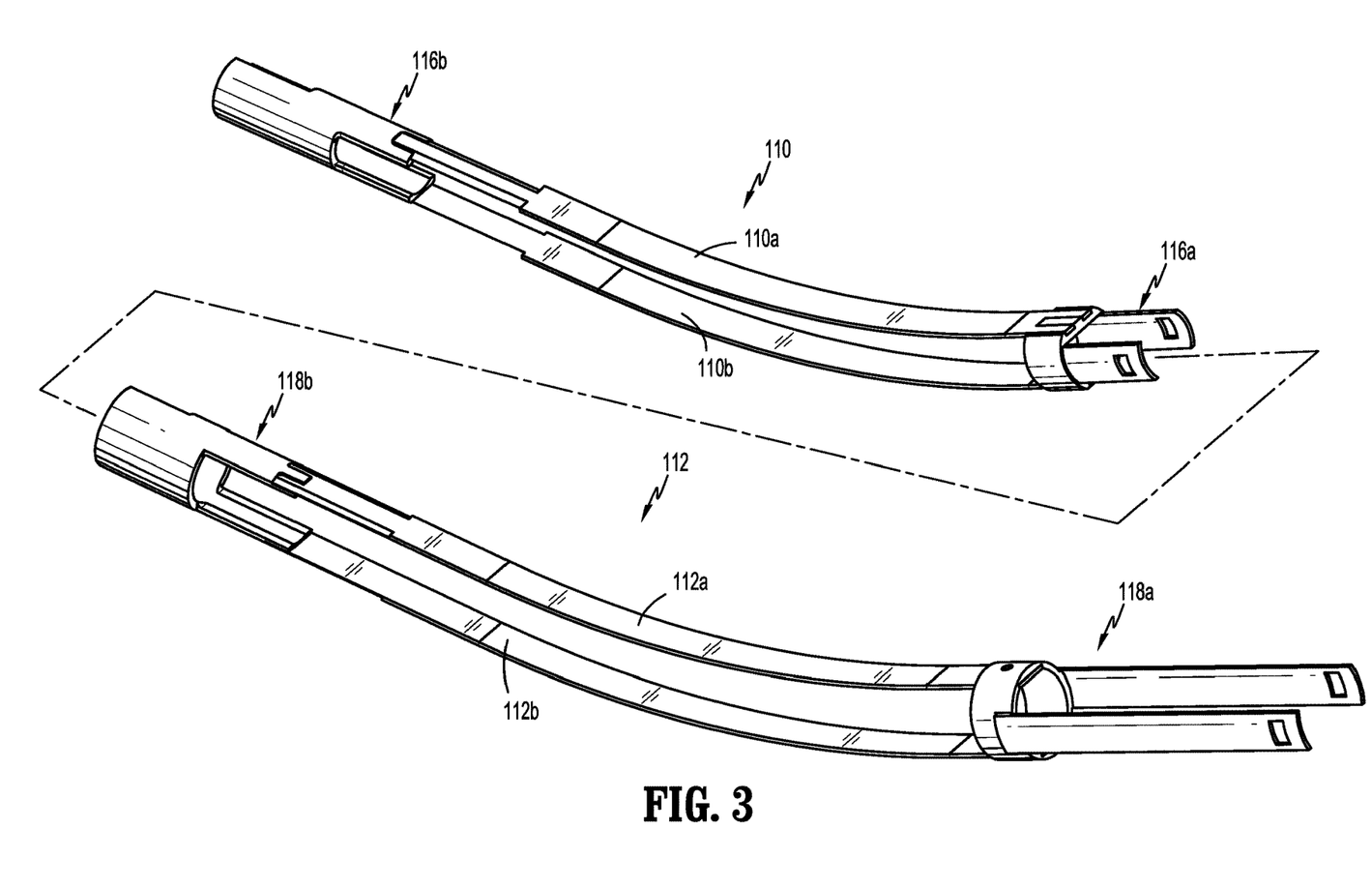
FIG. 3 is a perspective view of a drive assembly of the adapter assembly shown in FIG. 1 with components separated.

FIG. 3 illustrates the inner and outer drive assemblies 110, 112 of the distal portion 104 of the adapter assembly 100. The inner drive assembly 110 includes first and second drive members or flexible bands 110a, 110b supported on a proximal end by a proximal connector 116a and supported on the distal end by a distal connector 116b. The outer drive assembly 112 includes first and second drive members or flexible bands 112a, 112b supported on a proximal end by a proximal connector 118a and supported on a distal end by a distal connector 116b. The proximal connectors 116a, 118a of the respective inner and outer drive assemblies 110, 112 are operably connected to first and second drive members (not shown) in the proximal portion 102 of the adapter assembly 100. The distal connectors 116b, 118b of the respective inner and outer drive assemblies 110, 112 are operably connected to the loading unit 30 (FIG. 1) for effecting first and second functions of the loading unit 30, e.g., stapling tissue, cutting tissue. For a detailed description of the structure and function of the inner and outer band assemblies 110, 112, please refer to the '254 patent.

Figure 4:
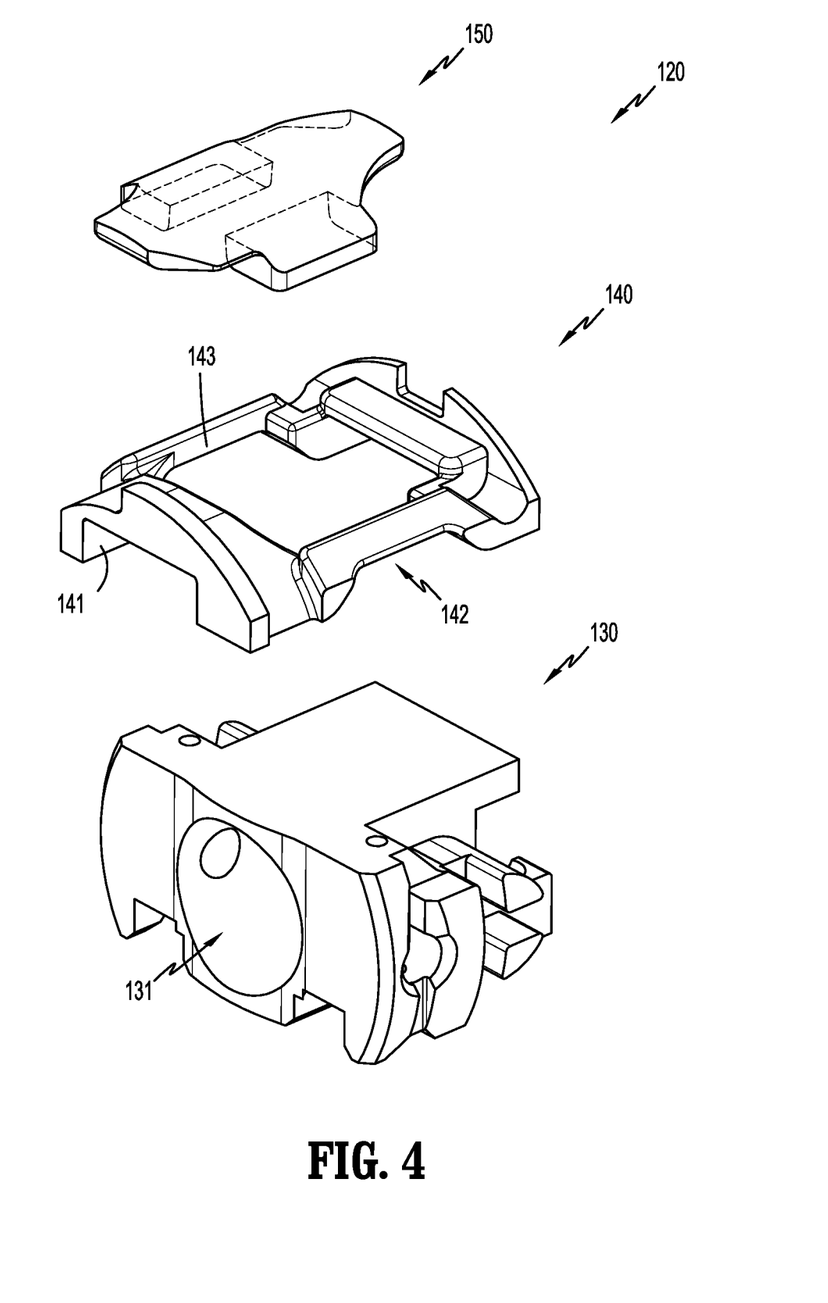
FIG. 4 is a perspective view of a trocar retaining mechanism of the adapter assembly shown in FIGS. 1 and 2 with parts separated.

FIG. 4 illustrates the trocar retaining mechanism 120 of the adapter assembly 100. The trocar retaining mechanism 120 is received within the distal portion 104 of the adapter assembly 100 to releasably retain the trocar assembly 50 within the distal portion 104 of the adapter assembly 100. The trocar retaining mechanism 120 is substantially similar to the trocar retaining mechanism described in U.S. Pat. App. Pub. No. 2020/0397475, and therefore will only be described in detail as relates to the differences therebetween.

The trocar retaining mechanism 120 includes a retaining block 130, an upper band guide 140, and a band support 150. The retaining block 130 defines a longitudinal opening 131 for receiving the trocar assembly 50. The upper band guide 140 includes a frame 142 defining a longitudinal cutout 141 for accommodating first flexible bands 110a (FIG. 8), 112a of the respective inner and outer band assemblies 110, 112. The upper band guide 140 further defines a central opening 143 configured to receive the band support 140.

Figures 5A, 5B:
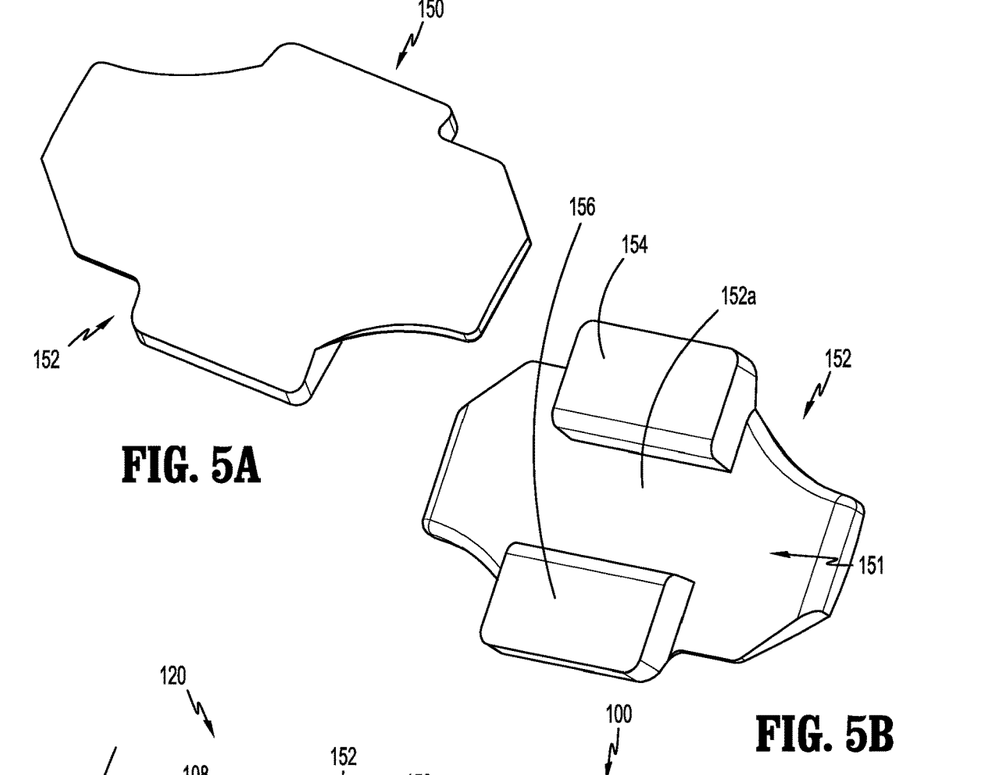
FIG. 5A is a side perspective view of a first side of a band support of the trocar retaining mechanism shown in FIG. 4.
FIG. 5B is side perspective view of a second side of the band support shown in FIG. 5A.

FIGS. 5A and 5B illustrate the band support 150 of the trocar retaining mechanism 120. The band support 150 includes a substantially planar body 152 that is supported within the central opening 143 of the upper band guide 140. First and second support members 154, 156 extend from a bottom surface 152a of the band support 150 and define a clearance 151 between the first and second support members 154, 156. The clearance 151 between the first and second support members 154, 156 accommodates a wire harness 108 (FIG. 6) of the adapter assembly 100.

Figure 6:
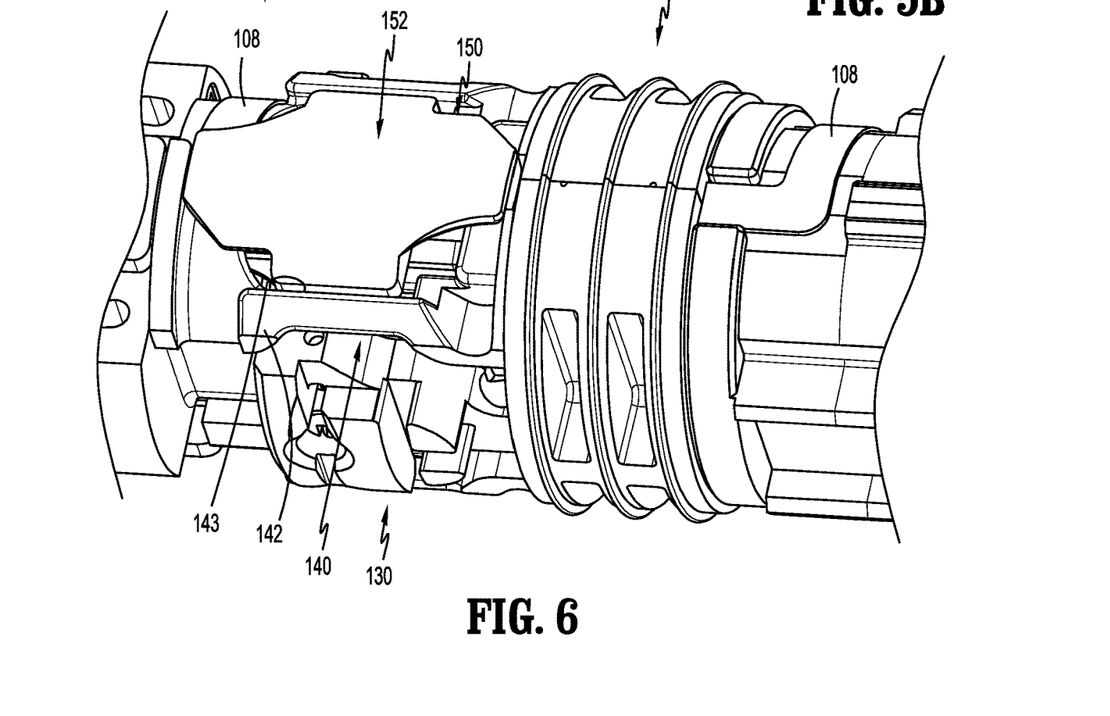
FIG. 6 is a perspective view of the trocar retaining mechanism shown in FIG. 4 supported in a distal portion of the adapter assembly shown in FIG. 2.
Figure 7:
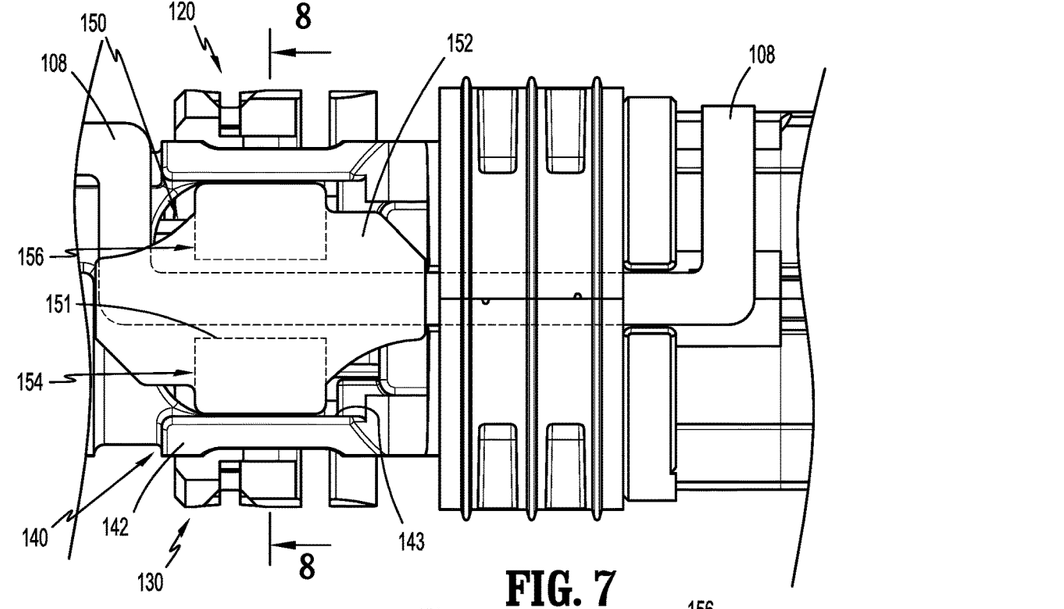
FIG. 7 is a side view of the trocar retaining mechanism supported in the adapter assembly as shown in FIG. 6.
Figure 8:
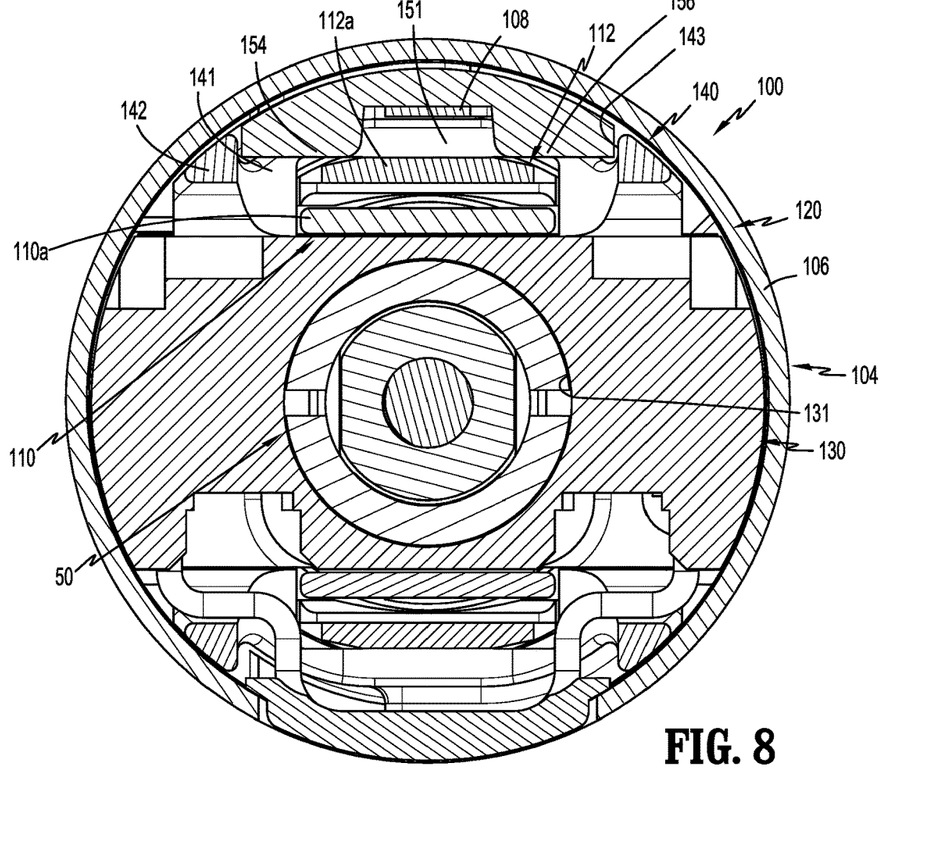
FIG. 8 is a cross-sectional end view taken along section line 8-8 shown in FIG. 7.

FIGS. 6-8 illustrate the trocar retaining mechanism 120 disposed within the distal portion 104 of the adapter assembly 100, including a trocar assembly 50 (FIG. 8) received through the retaining block 130 of the trocar retaining mechanism 120. The band support 150 is positioned within the central opening 143 of the upper band guide 140. The wire harness 108 extends through the clearance 151 between the first and second support members 154, 156 of the band support 152. The first flexible bands 110a, 112a of the respective inner and outer drive assemblies 110, 112 are received through the longitudinal cutout 141 in the upper band guide 130. The first and second support members 154, 156 of the band support 150 engage the first flexible band 112a of the outer drive assembly 112. In this manner, the band support 140 acts to prevent buckling of the first flexible band 112a during operation of the surgical stapling device 10 (FIG. 1). It is envisioned that, because of the close proximity of the first flexible band 112a of the outer drive assembly 112 to the first flexible band 110a of the inner drive assembly 110, the first flexible band 112a of the outer drive assembly 112 may assist in preventing buckling of the first flexible band 110a of the inner band assembly 110.

Figure 9:
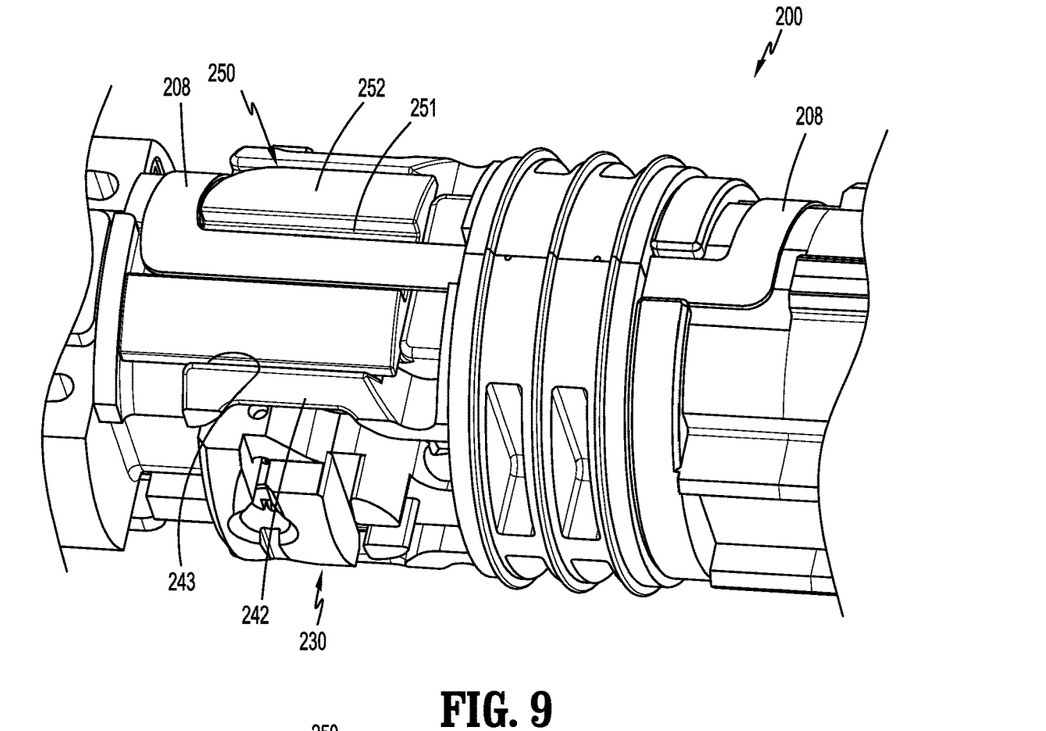
FIG. 9 is a perspective view of a trocar retaining mechanism according to another aspect of the disclosure, supported within a distal portion of an adapter assembly.

FIG. 9 illustrates an adapter assembly 200 including a trocar retaining mechanism according to another aspect of the disclosure, shown generally as trocar retaining mechanism 220. The trocar retaining mechanism 220 is substantially similar to trocar retaining mechanism 120 described above, and therefore, will only be described in detail as relates to the differences therebetween. The trocar retaining mechanism 220 includes a retaining block 230, an upper band guide 240, and a band support 250.

The retaining block 230 defines a longitudinal opening 231 (FIG. 12) for receiving the trocar assembly 50. The upper band guide 240 includes a frame 242 defining a longitudinal cutout 241 (FIG. 12) for accommodating first flexible bands 210a (FIG. 12), 212a of respective inner and outer band assemblies 210, 212. The upper band guide 240 further defines a central opening 243 configured to receive the band support 240.

Figures 10A, 10B:
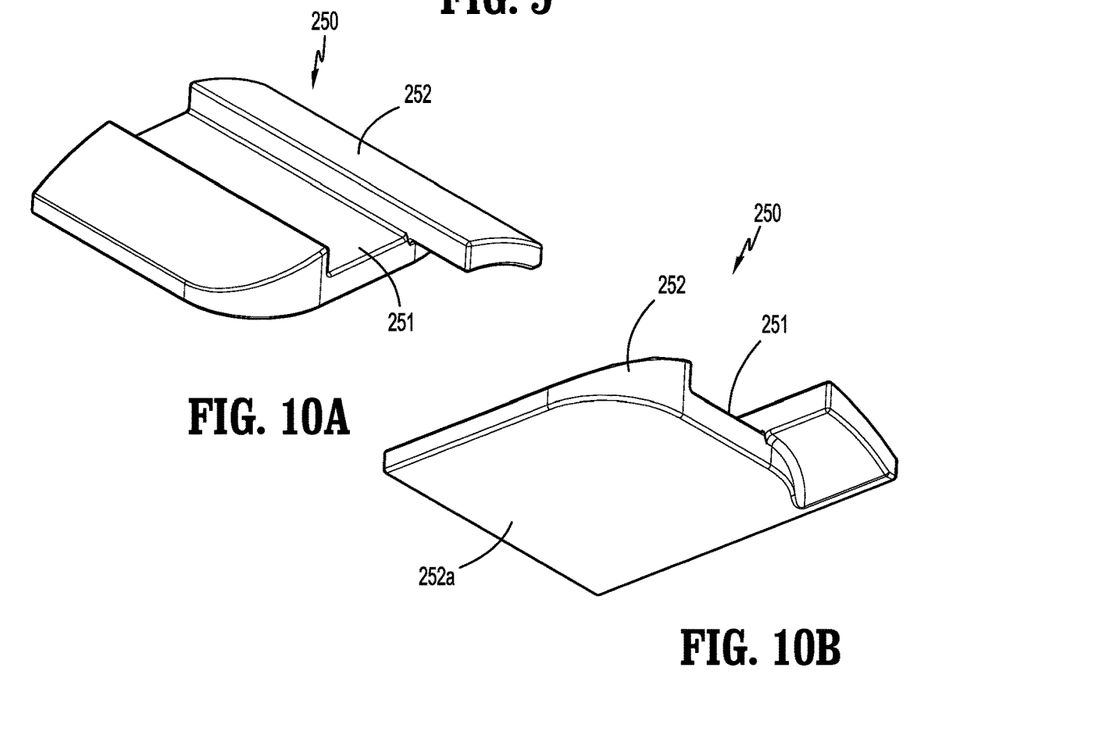
FIG. 10A is a side perspective view of a first side of a band support of the trocar retaining mechanism shown in FIG. 9.
FIG. 10B is side perspective view of a second side of the band support shown in FIG. 10A.
Figure 11:
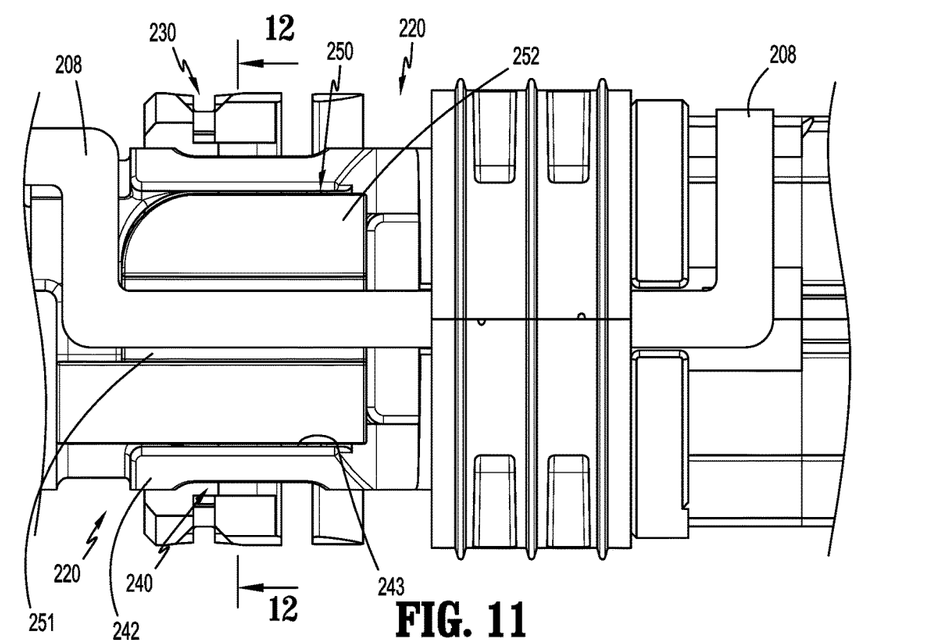
FIG. 11 is a side view of the trocar retaining mechanism supported in the adapter assembly as shown in FIG. 9.

FIGS. 10A and 10B illustrate the band support 250 of the trocar retaining mechanism 220. The band support 250 includes a substantially planar body 252 that is supported within the central opening 243 of the upper band guide 240. The band support 250 defines a channel 251 for accommodating a wire harness 208 (FIG. 9) of the adapter assembly 200. A bottom surface 252a of the band support 250 is configured to engage the first flexible band 212a of the outer drive assembly 212.

Figure 12:
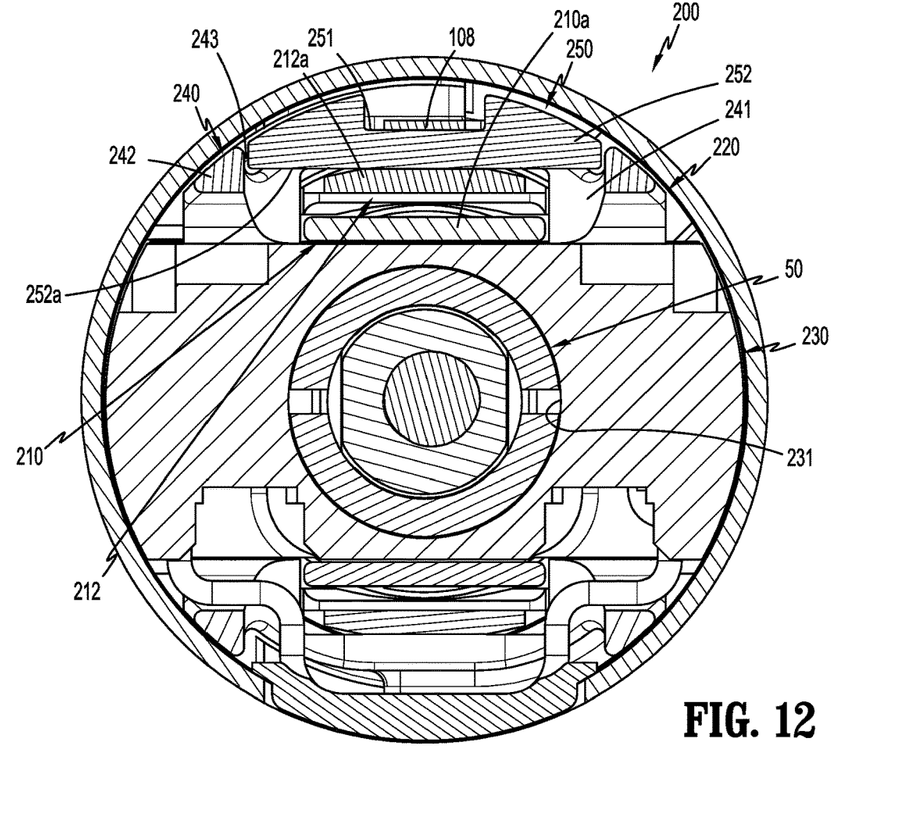
FIG. 12 is a cross-sectional end view taken along section line 12-12 shown in FIG. 11.

FIG. 12 illustrates the bottom surface 252a of the band support 250 in engagement with the first flexible band 212a of the outer drive assembly 212. The engagement of the bottom surface 252a of the band support 250 with the first flexible band 212a prevents buckling of the first flexible band 212a during operation of the surgical stapling device 10 (FIG. 1).

Figure 13:
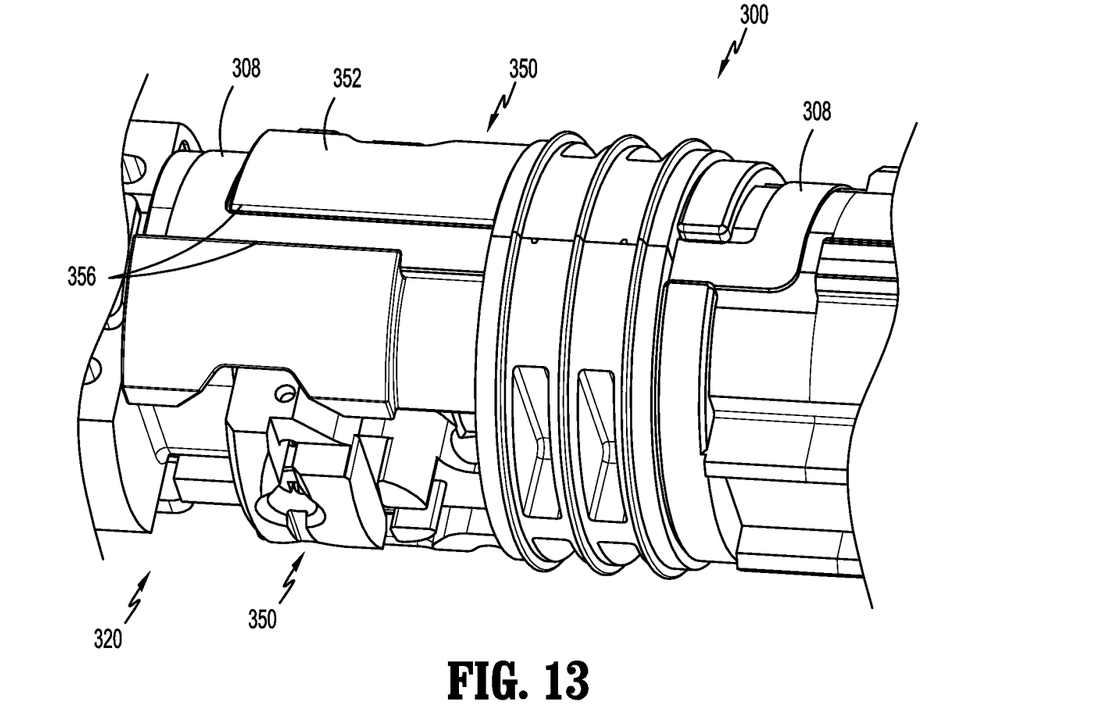
FIG. 13 is a perspective view of a trocar retaining mechanism according to another aspect of the disclosure, supported within a distal portion of an adapter assembly.

FIG. 13 illustrates an adapter assembly 300 including a trocar retaining mechanism according to another aspect of the disclosure, shown generally as trocar retaining mechanism 320. The trocar retaining mechanism 320 is substantially similar to trocar retaining mechanisms 120, 220 described above, and therefore, will only be described in detail as relates to the differences therebetween. The trocar retaining mechanism 320 includes a retaining block 330 and a band support 350. The retaining block 330 defines a longitudinal opening 331 (FIG. 16) for receiving the trocar assembly 50.

Figure 14A:
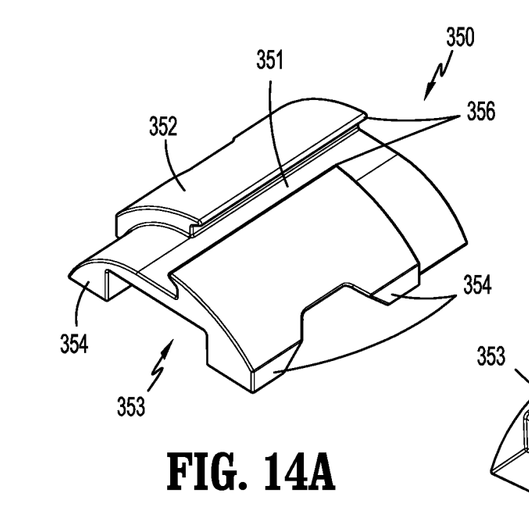
FIG. 14A is a side perspective view of a first side of a band support of the trocar retaining mechanism shown in FIG. 13.
Figure 14B:
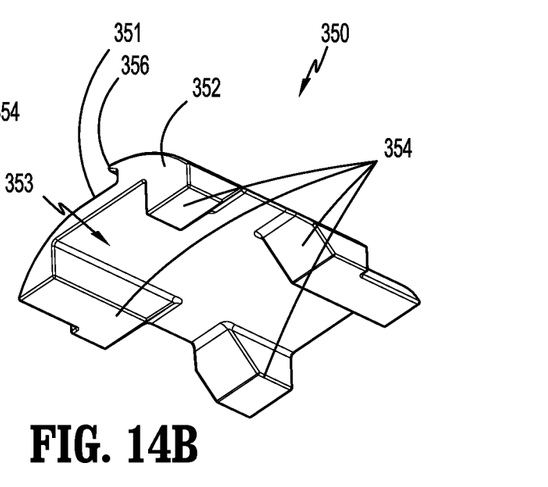
FIG. 14B is side perspective view of a second side of the band support shown in FIG. 14A.
Figure 16:
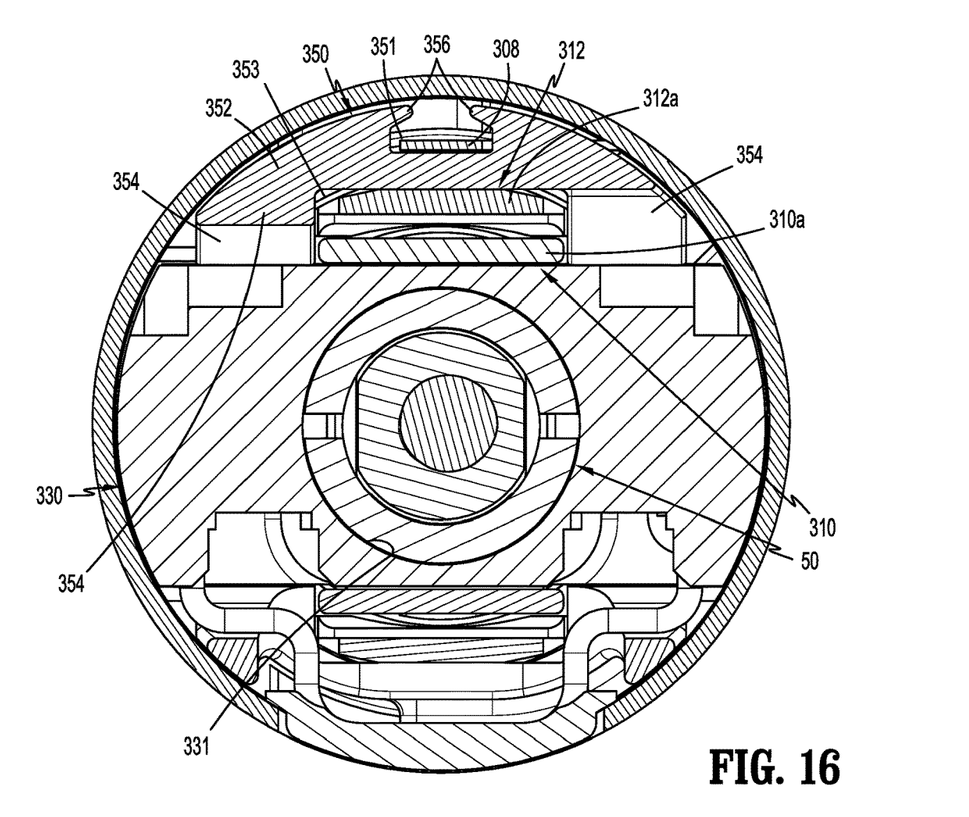
FIG. 16 is a cross-sectional end view taken along section line 16-16 shown in FIG. 15.

FIGS. 14A and 14B illustrate the band support 350 of the trocar retaining mechanism 320. The band support 350 includes a body 352 and a plurality of support members 354 extending from a bottom surface 352a of the body 352. The plurality of support members 354 are configured maintain the band support 350 adjacent the retaining block 330 (FIG. 16). The band support 350 defines a first channel 351 for accommodating a wire harness 308 (FIG. 9) of the adapter assembly 300. A lip 356 on either side of the first channel 351 operates to maintain the wire harness 308 relative to the band support 350 during operation of the surgical stapling device 10 (FIG. 1). The band support 350 further defines a second channel 353 between the plurality of support members 354 for accommodating first flexible bands 310a (FIG. 16), 312a of respective inner and outer band assemblies 310, 312. The bottom surface 352a of the band support 350 is configured to engage the first flexible band 212a of the outer drive assembly 212.

Figure 15:
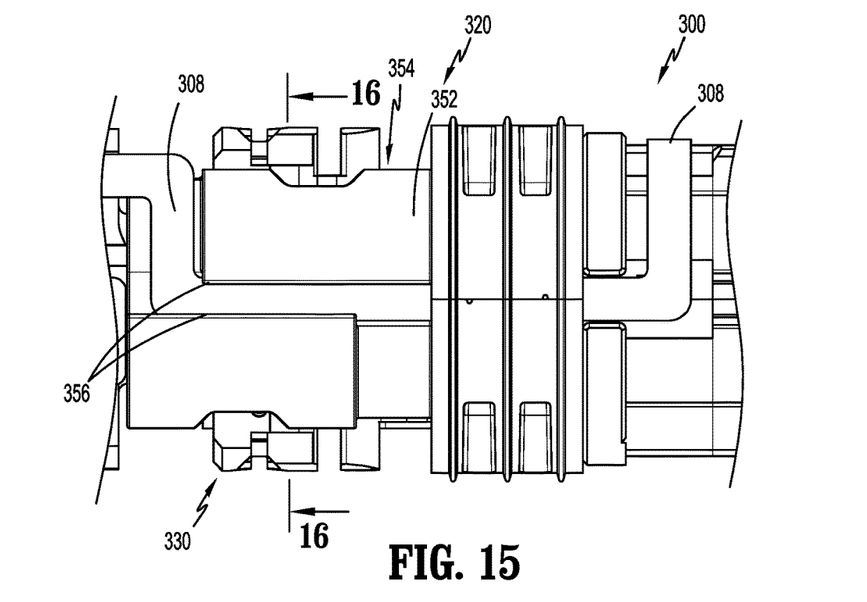
FIG. 15 is a side view of the trocar retaining mechanism supported in the adapter assembly as shown in FIG. 13.

FIGS. 15 and 16 illustrates the first flexible bands 310a, 312b of the inner and outer drive assemblies 310, 312 received within the second channel 353 of the band support 350, with the bottom surface 352a of the band support 350 in engagement with the first flexible band 312a. The engagement of the bottom surface 352a of the band support 350 with the first flexible band 312a prevents buckling of the first flexible band 312a during operation of the surgical stapling device 10 (FIG. 1).

Persons skilled in the art will understand that the devices and methods specifically described herein and illustrated in the accompanying drawings are non-limiting, exemplary devices. It is envisioned that the elements and features illustrated or described in connection with one exemplary device may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. An adapter assembly for connecting a loading unit to a handle assembly, the adapter assembly comprising:
   a sleeve;
   a trocar assembly releasably securable with the sleeve;
   a drive assembly including at least one flexible band extending at least partially within the sleeve; and
   a trocar retaining mechanism configured to releasably secure the trocar assembly within the sleeve, the trocar retaining mechanism including a retaining block for receiving the trocar assembly therethrough and a band support disposed outward of the retaining block, the band support positioned in engagement with the at least one flexible band to prevent buckling of the at least one flexible band.

2. The adapter assembly of claim 1, wherein the band support includes a bottom surface in engagement with the at least one flexible band.

3. The adapter assembly of claim 1, wherein the band support includes first and second support members in engagement with the at least one flexible band.

4. The adapter assembly of claim 1, wherein the band support includes a cutout for accommodating the at least one flexible band.

5. The adapter assembly of claim 1, further including a wire harness extending at least partially through the sleeve, wherein the band support defines a channel for receiving the wire harness.

6. The adapter assembly of claim 5, wherein the band support includes a lip on either side of the channel for maintaining the wire harness within the channel.

7. The adapter assembly of claim 1, wherein the trocar retaining mechanism further includes a band guide defining a cutout for receiving the at least one flexible band.

8. The adapter assembly of claim 7, wherein the band guide defines a central opening for receiving the band support.

9. The adapter assembly of claim 7, wherein the trocar retaining mechanism further includes a retaining block defining a longitudinal passage for receiving the trocar assembly.

10. The adapter assembly of claim 1, wherein the trocar assembly includes a housing and a trocar member slidably disposed within the trocar assembly.

11. A surgical stapling device comprising:
    a handle assembly; and
    an adapter assembly secured to the handle assembly, the adapter assembly including,
        a drive assembly including at least one flexible band extending at least partially through the adapter assembly; and a trocar retaining mechanism configured to releasably secure the trocar assembly within the sleeve, the trocar retaining mechanism including a retaining block for receiving the trocar assembly therethrough and a band support disposed outward of the retaining block, the band support positioned in engagement with the at least one flexible band to prevent buckling of the at least one flexible band.

12. The surgical stapling device of claim 11, wherein the band support includes a bottom surface in engagement with the at least one flexible band.

13. The surgical stapling device of claim 11, wherein the band support includes first and second support members in engagement with the at least one flexible band.

14. The surgical stapling device of claim 11, wherein the band support includes a cutout for accommodating the at least one flexible band.

15. The surgical stapling device of claim 11, further including a wire harness extending at least partially through the adapter assembly, wherein the band support defines a channel for receiving the wire harness.

16. The surgical stapling device of claim 15, wherein the band support includes a lip on either side of the channel for maintaining the wire harness within the channel.

17. The surgical stapling device of claim 11, wherein the retaining mechanism further includes a band guide defining a cutout for receiving the at least one flexible band.

18. The surgical stapling device of claim 17, wherein the band guide defines a central opening for receiving the band support.

19. The surgical stapling device of claim 17, further including a trocar assembly, wherein the retaining mechanism includes a retaining block defining a longitudinal passage for receiving the trocar assembly.

20. The surgical stapling device of claim 11, wherein the trocar assembly includes
a housing and a trocar member slidably disposed within the trocar assembly.

* * * * *